(12) United States Patent
McMurray et al.

(10) Patent No.: US 10,400,577 B2
(45) Date of Patent: Sep. 3, 2019

(54) METHOD AND APPARATUS FOR SELECTING DIVERSION MATERIAL FOR A WELLBORE OPERATION

(71) Applicant: STEP ENERGY SERVICES LTD., Calgary (CA)

(72) Inventors: Andrew James McMurray, Calgary (CA); Darren Michael Maley, Calgary (CA); Michael Edward Burvill, Sylvan Lake (CA); Bailey Todd Epp, Airdrie (CA)

(73) Assignee: STEP ENERGY SERVICES LTD., Calgary (CA)

( * ) Notice: Subject to any disclaimer, the term of this patent is extended or adjusted under 35 U.S.C. 154(b) by 297 days.

(21) Appl. No.: 15/411,944

(22) Filed: Jan. 20, 2017

(65) Prior Publication Data

US 2017/0211373 A1 Jul. 27, 2017

Related U.S. Application Data

(60) Provisional application No. 62/281,482, filed on Jan. 21, 2016.

(51) Int. Cl.
*E21B 47/06* (2012.01)
*G01N 15/08* (2006.01)
*E21B 33/138* (2006.01)

(52) U.S. Cl.
CPC ......... *E21B 47/06* (2013.01); *G01N 15/0826* (2013.01); *E21B 33/138* (2013.01)

(58) Field of Classification Search
CPC .... E21B 33/138; E21B 47/06; G01N 15/0826
See application file for complete search history.

(56) References Cited

U.S. PATENT DOCUMENTS 2,646,678 A * 7/1953 Standing ............... B01D 29/111
  210/212
2,733,595 A * 2/1956 Twining ................ E21B 21/003
  210/289

(Continued)

OTHER PUBLICATIONS

Pinnacle, Technologies, Inc., "Evaluation of Oil-Industry Stimulation Practices for Engineered Geothermal Systems" Oct. 2007.*

(Continued)

*Primary Examiner* — John Fitzgerald
(74) *Attorney, Agent, or Firm* — Christensen O'Connor Johnson Kindness, PLLC (57) ABSTRACT

Diversion material is particulate material used during wellbore treatment to temporarily seal a wellbore fluid passage such as a fracture. A method and apparatus for diversion material testing permits simulation of wellbore fracture parameters and testing thereof against a selected diversion material. The apparatus comprises: a fluid piping system including a fluid inlet end and a fluid outlet end; a fracture simulator chamber including a fracture-simulating outlet slot through a wall of the chamber, the fracture simulator chamber being releasably connectable to the fluid outlet end; a pump to pump fluid through the fluid piping system from the fluid inlet line to the fluid outlet end and into the fracture simulator chamber; a diversion material launch system connected in communication with the fluid piping system between the fluid inlet end and the fluid outlet line; and a pressure transducer in the fluid piping system to measure pressure in the fluid piping system.

29 Claims, 7 Drawing Sheets

(56) References Cited

U.S. PATENT DOCUMENTS

| | | | | |
|---|---|---|---|---|
| 6,543,276 | B2* | 4/2003 | Murphy, Jr. | G01N 15/08 |
| | | | | 73/61.63 |
| 7,900,504 | B2* | 3/2011 | Huynh | G01N 15/08 |
| | | | | 73/38 |
| 8,762,118 | B2* | 6/2014 | Nasreldin | E21B 43/26 |
| | | | | 703/10 |
| 8,863,567 | B2* | 10/2014 | Jappy | E21B 21/003 |
| | | | | 73/61.64 |
| 9,279,904 | B2* | 3/2016 | Brooks | E21B 43/11 |
| 9,285,355 | B2* | 3/2016 | Murphy | E21B 49/008 |
| 9,739,694 | B2* | 8/2017 | Amanullah | C09K 8/03 |
| 9,784,102 | B2* | 10/2017 | Blue | G01N 15/0806 |
| 10,180,063 | B2* | 1/2019 | Murphy | G01N 33/2823 |
| 2009/0065207 | A1* | 3/2009 | Shenoy | C09K 8/68 |
| | | | | 166/278 |
| 2011/0120217 | A1* | 5/2011 | Huynh | G01N 15/08 |
| | | | | 73/152.22 |
| 2011/0295509 | A1* | 12/2011 | Huynh | E21B 21/00 |
| | | | | 702/12 |
| 2014/0290937 | A1* | 10/2014 | Crews | E21B 43/26 |
| | | | | 166/250.1 |
| 2015/0135815 | A1* | 5/2015 | Blue | G01N 15/0806 |
| | | | | 73/152.18 |
| 2017/0138169 | A1* | 5/2017 | Bogdan | E21B 33/12 |

OTHER PUBLICATIONS

Schlumberger, "FracCade," 2010.*

* cited by examiner

Figure 6 ized, the
METHOD AND APPARATUS FOR SELECTING DIVERSION MATERIAL FOR A WELLBORE OPERATION

CROSS-REFERENCE TO RELATED APPLICATION

This application claims the benefit under 35 U.S.C. § 119(e) of U.S. Provisional Patent Application No. 62/281,482, filed Jan. 21, 2016, of which is incorporated by reference herein in its entirety.

FIELD OF THE INVENTION

The present invention relates to methods and apparatus and, in particular, for selection and testing of diversion material.

BACKGROUND

Diversion material is a particulate material used during wellbore treatment operations to temporarily seal a fluid passage, such as a fracture in a wellbore operation. In particular, diversion material may be conveyed downhole and placed against or within a fluid passage to create a seal against the fluid passage. The diversion material is selected to be slightly soluble in wellbore conditions such that with residence time downhole, the seal created by the diversion material solubilizes to reopen the fluid passage. The solubilized diversion material can then be produced back. Diversion material is sometimes referred to as diverter, a bridging agent, a temporary degradable particulate or solid production chemical.

Diversion material is entrained in wellbore treatment fluids and it is intended to be forced into wellbore fractures to prevent fluid loss to that area of the wellbore. Diversion material is available in different particle sizes and shapes, often categorized by mesh size. Diversion material is also available with different degradation properties based to residence time and wellbore conditions temperature.

Diversion material testing is difficult and oftentimes the testing is done directly in the wellbore. In-wellbore testing is not ideal, as it is less difficult to validate performance, technology and treatment plans.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The invention relates to methods and apparatus for testing of diversion material for wellbore applications.

In accordance with a broad aspect of the invention, there is provided an apparatus for testing wellbore materials comprising: a fluid piping system including a fluid inlet end and a fluid outlet end; a fracture simulator chamber including a fracture-simulating outlet slot through a wall of the chamber, the fracture simulator chamber being releasably connectable to the fluid outlet end; a pump to pump fluid through the fluid piping system from the fluid inlet line to the fluid outlet end and into the fracture simulator chamber; a diversion material launch system connected in communication with the fluid piping system between the fluid inlet end and the fluid outlet line; and a pressure transducer in the fluid piping system to measure pressure in the fluid piping system In accordance with another aspect of the invention, there is provided a method for testing the efficiency of a diversion material with respect to a wellbore fracture profile comprising: injecting a diversion material with a known particle size through a test apparatus including through a fracture simulator; and monitoring pressure conditions in the test apparatus to identify an increase in pressure indicative of a fluid blockage formed in the fracture simulator by the diversion material It is to be understood that other aspects of the present invention will become readily apparent to those skilled in the art from the following detailed description, wherein various embodiments of the invention are shown and described by way of illustration. As will be realized, the invention is capable for other and different embodiments and its several details are capable of modification in various other respects, all without departing from the spirit and scope of the present invention. Accordingly, the drawings and detailed description are to be regarded as illustrative in nature and not as restrictive.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

Referring to the drawings, several aspects of the present invention are illustrated by way of example, and not by way of limitation, in detail in the figures.

DETAILED DESCRIPTION OF THE VARIOUS EMBODIMENTS

The detailed description set forth below in connection with the appended drawings is intended as a description of various embodiments of the present invention and is not intended to represent the only embodiments contemplated by the inventor. The detailed description includes specific details for the purpose of providing a comprehensive understanding of the present invention. However, it will be apparent to those skilled in the art that the present invention may be practiced without these specific details.

A fracture profile of a wellbore may be known including any one or more fracture parameters such as fracture dimensions such a fracture width, length or depth. Based on the type of formation (i.e. carbonate, shale, sandstone, etc.) it is possible to characterize another fracture profile parameter: surface roughness. The fracture orientation can also be established to determine another aspect of the fracture profile. The orientation may include parameters such as the number of fractures in an area and orientation of the fracture length relative to the wellbore axis (i.e. axially extending, circumferentially extending, etc.).

It has been determined that, depending on a fracture profile, some diversion material particle sizes work better than others. The present invention offers a method and apparatus for selecting and validating the usefulness of a diversion material or a selected series or blend of diversion materials for a particular fracture profile. An appropriate diversion material profile such as, for example, a diversion material chemical or particle size, a blend of diversion materials including with a particle size distribution, a series of diversion materials (i.e. a plan), an amount and/or a volume of diversion material may be determined for a particular fracture profile.

Alternately, the method and apparatus may be used to validate the suitability of new diversion materials, blends and program plans.

The apparatus can be operated in a manner to emulate wellbore conditions and launch conditions.

In one embodiment, a method and apparatus is provided to test the efficiency of a diversion material with respect to a selected fracture profile including a fracture size such as a fracture width.

In the method, a diversion material with a known particle size is injected at process conditions similar to, for example scaled to, known fracturing conditions through a test apparatus, including through a fracture simulator, while the process conditions in the test apparatus are monitored. The process conditions being monitored indicate the bridging of diversion material particles and the back pressure based on particle size.

Figure 1:
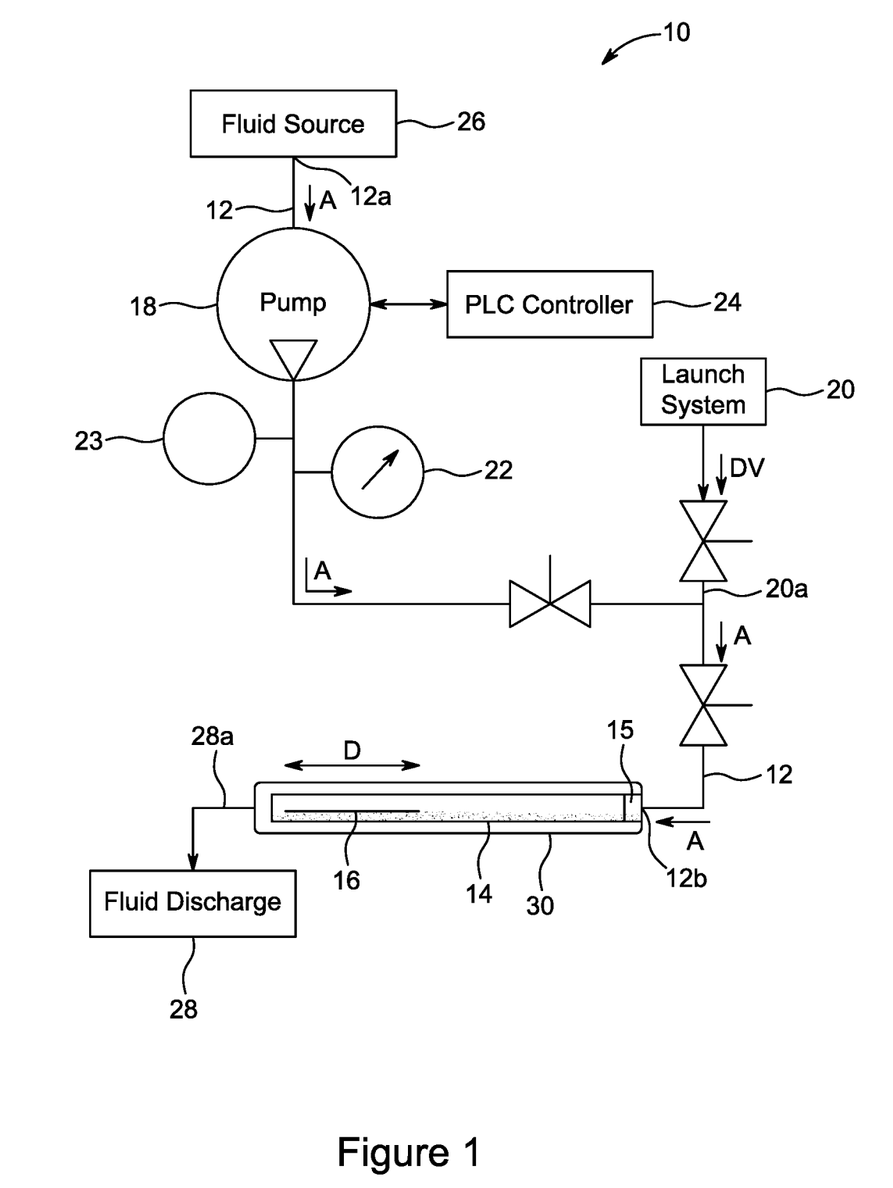
FIG. 1 is a schematic diagram of a diversion material testing apparatus.

A possible test apparatus 10 is shown in FIG. 1. Apparatus 10 includes a fluid piping system 12 including a fluid inlet end 12a and a fluid outlet end 12b and a fracture simulator at the fluid outlet end 12b.

Figures 3A, 3B:
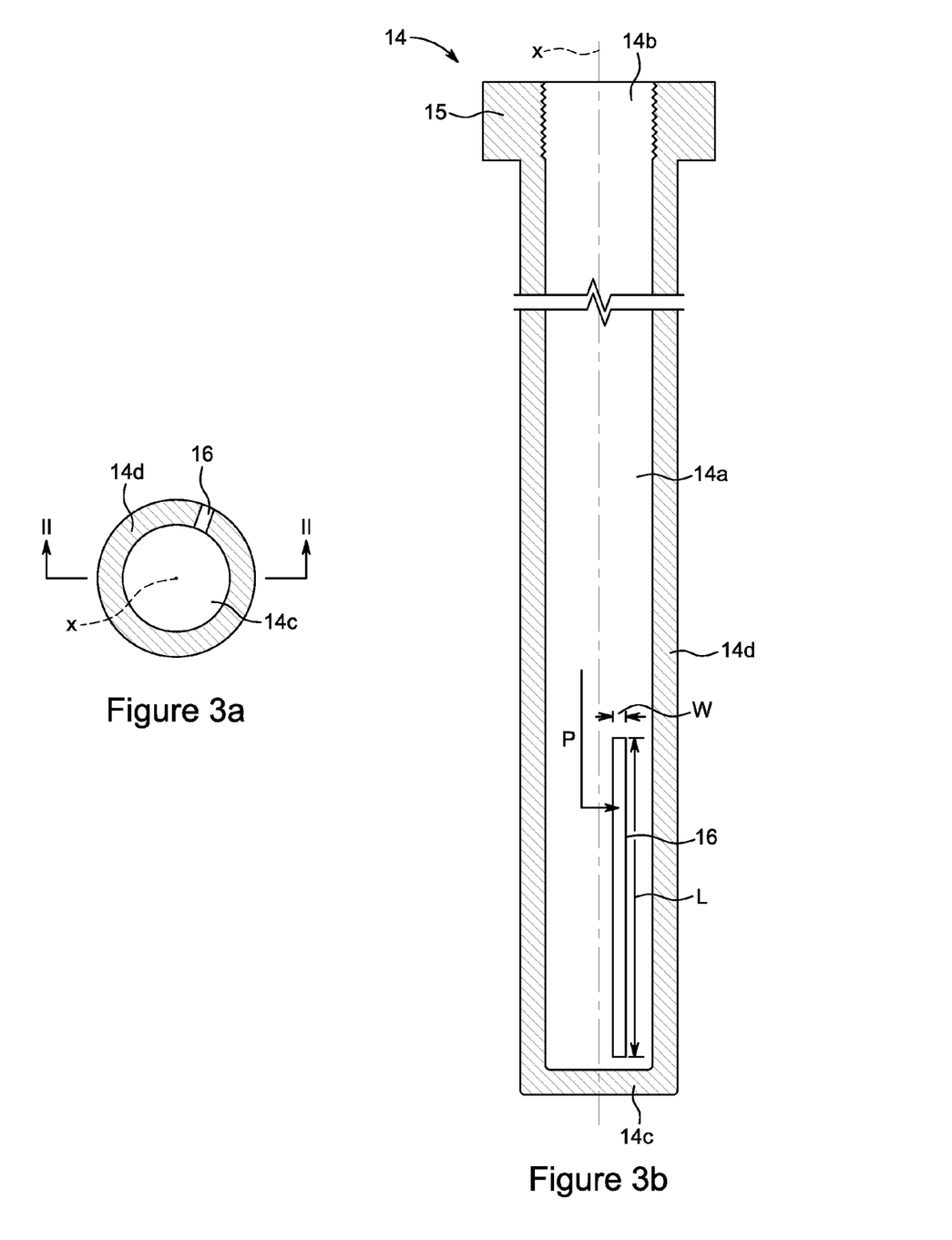
FIG. 3*a* is a sectional view of a fracture simulator along line I-I of FIG. 2.
FIG. 3*b* is a sectional view along line II-II of FIG. 3*a;*

With reference also to FIGS. 3a and 3b, fracture simulator 14, includes therein a fracture simulator chamber 14a and a fracture-simulating outlet slot 16 through a wall that defines the chamber. Fracture simulator 14 is releasably connectable, as by a releasable connection 15 to the fluid outlet end of the fluid piping system and is connected in fluid communication with the fluid piping system to receive fluid from the outlet end into the chamber 14a.

As is typical for a slot, slot 16 has edges that define an opening in the shape of a rectangle with a length dimension L and a width dimension W, which is smaller than the length. This rectangular shape is useful to simulate a wellbore fracture, since a fracture also has a length and a width, where the width is smaller than the length. The slot characteristics, such as its dimensions and its orientation, can be defined and recorded for each fracture simulator, as will be appreciated by further description herein below. Apparatus 10 may have more than one fracture simulator 14 with differing slot dimensions and features. The releasable connection 15 facilitates installation and removal for interchanging simulators 14 on end 12b.

The diameter of the sidewall 14b, which thereby defines inner diameter across chamber 14a, can be scaled based on hole dimensions. However, it is not necessary to duplicate the hole dimensions, as the process conditions can be accommodated to simulate wellbore fracturing conditions without using a fracture simulator that matches the hole inner diameter. While the best testing apparatus would have the same size as the wellbore casing/hole size in which the diversion material is to be employed, typically conditions within a larger diameter hole can be simulated adequately even using a smaller diameter fracture simulator.

The apparatus further includes a pump 18 to pump fluid through the fluid piping system from the fluid inlet end 12a to the fluid outlet end 12b and into the fracture simulator's chamber 14a. The pump is configured to pump fluid through piping 12 from source through the pump into fracture simulator 14 at rates scalable to rates employed in wellbore operations. For example, pump 18 is capable of operation to generate continuous flow and capable of inducing turbulence in fluid flow at least at fracture simulator. The method includes pumping at a rate, for example between 20-60 l/m, to induce turbulence in the fluid flowing through the fracture simulator to simulate the flow during wellbore fracturing operations. The pumping can be maintained continuously over a period of time for prolonged testing or to pump more than one pill.

A diversion material launch system 20 is connected in fluid communication with the fluid piping system between the fluid inlet end and the fluid outlet line. The diversion material launch system is configured to launch, arrow DV, diversion material into the fluid piping system so that it can be entrained in the fluid passing through the apparatus toward the fracture simulator. The diversion material launch system may take many forms, for example with supply tanks, injection mechanisms, etc. In one embodiment, system 20 introduces the diversion material by gravity, suction, back pressure, valving, etc. from a supply line 20a into fluid piping 12.

A pressure transducer 22 in the fluid piping system is configured to measure pressure in the fluid piping system. Optionally, the apparatus may further include a flow meter 23 or and/or a controller such as a programmable logic controller (PLC) 24. The flow meter and/or pressure transducer measure process conditions within the apparatus, for example, fluid conditions such as a flow rate and pressure. The PLC 24 can monitor overall conditions and feedback to the pump 18, for example, to shut down the pump if pressure increases to a set level.

Apparatus 10 may include or receive connection to a fluid source 26 at the inlet end 14a. Likewise, a fluid discharge 28, such as may include a receptacle such as a pan or tank, can be provided to receive fluid passing from slot 16 of fracture simulator 14. The fluid can be a fluid used in actual wellbore fracturing such as liquid (i.e. water, gel, hydrocarbon, etc.) or gas (i.e. nitrogen, hydrocarbon, etc.) Depending on the fluid being used and general apparatus operations, fluid may openly flow to discharge 28 or may be passed through a contained discharge line 28a. To best simulate downhole fracture conductivity conditions, the discharge components 28, 28a are at some point open to ambient.

Apparatus 10 is configured to move fluid, arrow A, from the fluid inlet end to the fluid outlet end, to load an amount of a diversion material from the diversion material launch system into the fluid and to move the diversion material into the fracture simulator chamber, while monitoring the pressure for a pressure increase indicative of the diversion material blocking the fracture-simulating slot 16.

In any test, one amount of diversion material, which is sometimes referred to as a "pil," can be launched and pumped into the fracture simulator while pressure is monitored or a series of amounts (i.e. pills) of diversion material or other materials can be launched and monitored. In a test including series of pills, the pills of diversion material can all be the same type/concentration of diversion materials or all or some of the pills can be of other types.

Figure 2:
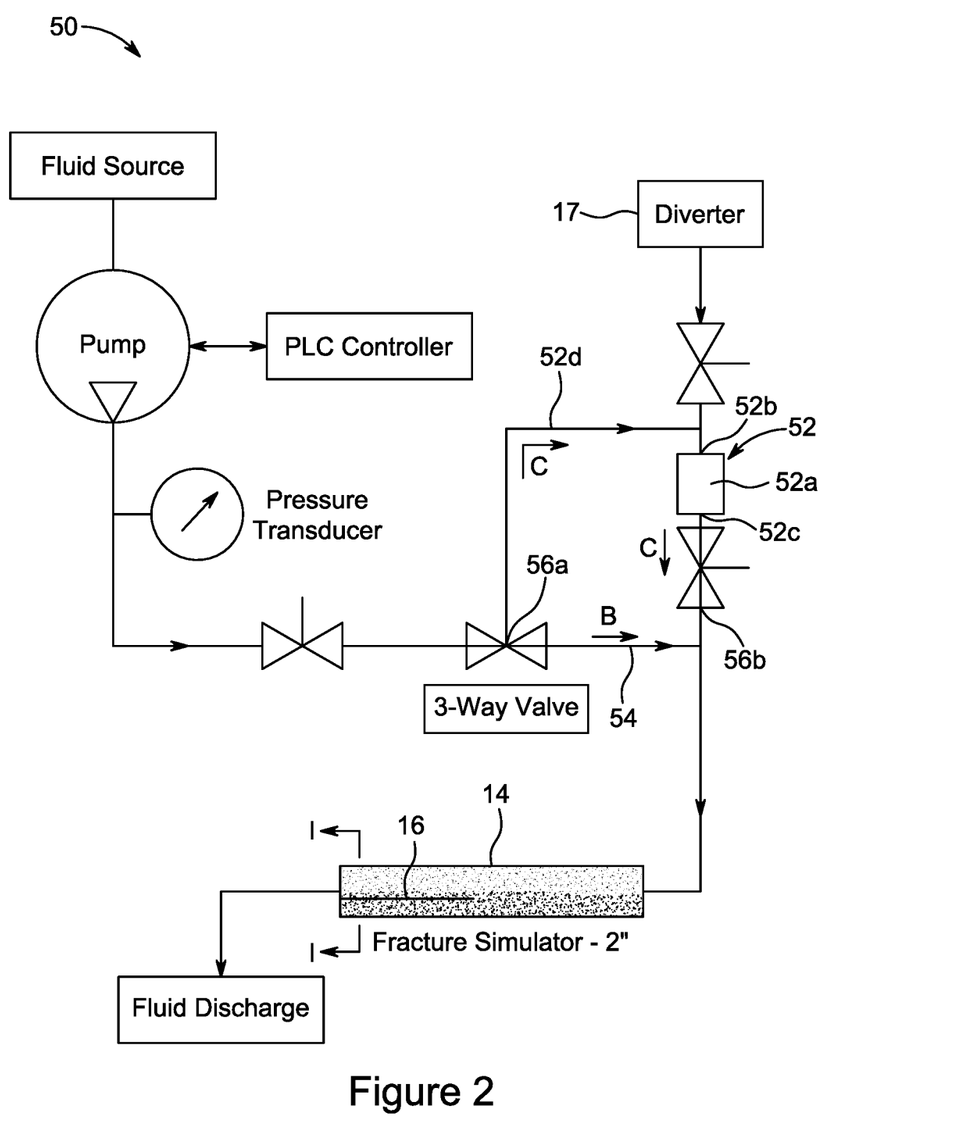
FIG. 2 is a schematic diagram of another diversion material testing apparatus.

Another test apparatus 50 is shown in FIG. 2. The apparatus is similar to that of FIG. 1. However, apparatus 50 has options that can be employed each alone or in combination. Notable options include an in-line material launcher 52 and a by-pass loop 52d.

In-line material launcher 52 includes a chamber 52a that can accommodate diversion material and an inlet 52b connected to upstream fluid piping and an outlet 52c connected to downstream fluid piping. Process fluid can be introduced to the chamber via inlet 52b to entrain the diversion material contained therein and then process fluid with entrained diversion material can exit the chamber and flow towards the fracture simulator 14. Apparatus 50 can include a diversion material supply tank 17 connected by a line and valve to the launcher 52. The diversion material can be loaded to the launcher from the supply tank 17, permitting each pill in a series of pills to be prepared and can be loaded from supply tank 17 to chamber 52a one at a time.

By-pass loop 52d is a piping line that by-passes direct line 54 to the simulator and permits fluid communication with launcher 52. Direct line 54 extends to provide communication between the inlet end and the outlet end of the piping 12 without passing through the launcher. Valves 56a, 56b, such as three-way valve 56a permit selection of the fluid path either through direct line 54 or through by-pass loop and launcher 52.

The apparatus contains three-way valve 56a and fitting arrangement such that flow can either flow directly to the wellhead or by-pass to the diverter material launching section. Thus, in a method to pump fluid from fluid source 26 to fracture simulator 14, the operator can establish a control, baseline pressure, arrow B, prior to reconfiguring the valve 56a to permit flow through the diverter material launching section, arrow C, to launch diverter. In addition or alternately, valve 56a can be actuated to direct flow through the direct line 54 when testing the effects of launching multiple pills in sequence. Flow can be continuous through the fracture simular by directing flow through the direct line 54 while the next pill is being loaded from tank 17 to launcher 52. After the next pill is loaded, valve 56a can be selected to open flow through line 52d to launcher 52. Thus it is possible to pump pills on the fly in sequence until the desired performance result is achieved or the test is otherwise complete.

The apparatus, for example as shown in FIG. 1 or 2, permits the use of various fracture simulators to simulate wellbore fracture conditions. It is even noted that the fracture simulator 14 of FIG. 1 differs from that of FIG. 2 and there are even further options such as those shown in FIGS. 3a-5c.

The fracture simulator includes a releasable connection 15 at its inlet end through which it is securely but releasably connected in a pressure tight manner onto the outlet end of the piping. The releasable connection, for example, may be a threaded, quick release or flanged connection.

The releasable connection facilitates removal and replacement of one type of fracture simulator with another type. For example, one fracture simulator of a known geometry can be quickly replaced with another fracture simulator of a known but different geometry, for example each having a different slot width to each simulate a corresponding fracture width. In one embodiment, for example, an apparatus may include a plurality of fracture simulators each similar in many ways, for example with similar releasable connectors, length, inner diameter, but with different slot characteristics (i.e. dimensions, roughness or orientations). A fracture simulator may therefore be selected from the plurality of fracture simulators for installation onto the test apparatus based on desired slot characteristics against which the diversion material is to be tested. The selected slot characteristic such as width may be that to correspond with a known fracture condition, such as fracture width, such as according to the formation's fracture profile in which the diversion material to be tested is intended to be used.

Figure 3C:
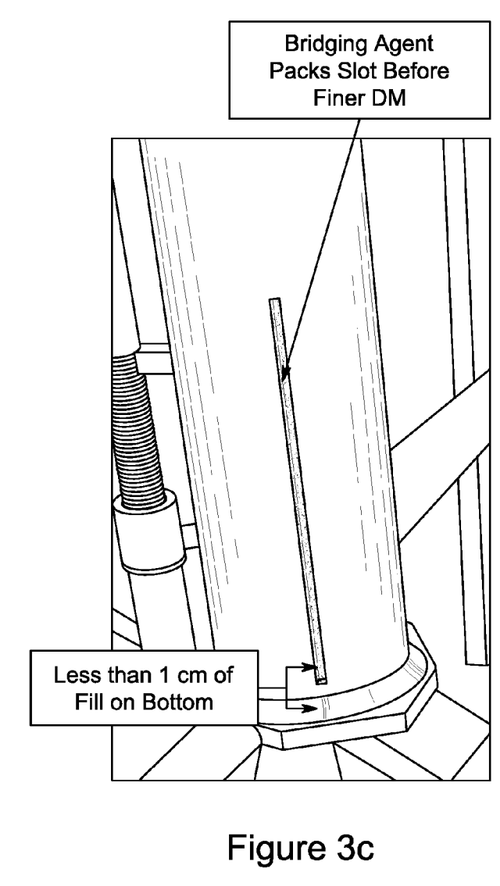
FIG. 3*c* is a photo of a fracture simulator similar to that of FIG. 3*a* after a test with diversion material forming a seal therein.
Figure 3D:
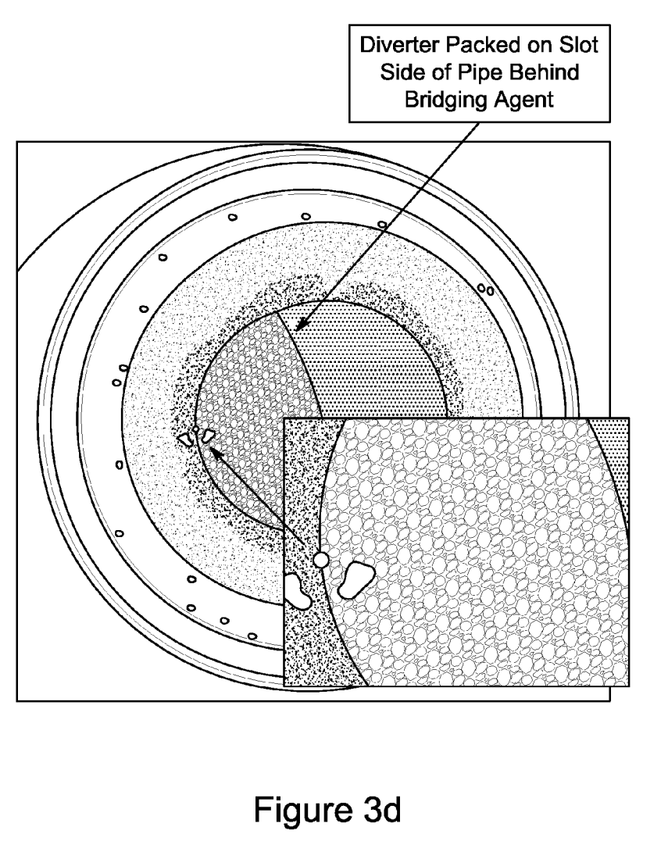
FIG. 3*d* is a photo of a top view through the upper end of the fracture simulator of FIG. 3*c;*

As shown in FIGS. 2-3d, a basic fracture simulator 14 has a wall that defines therewithin a fracture simulator chamber 14a and a fracture-simulating outlet slot 16 through the wall. The fracture simulator chamber is configured to define a flow path for fluid from its inlet end 14b, along a long axis x and then substantially perpendicularly relative to axis x, toward the slot. As such, fluid passing through the chamber, arrow P, is redirected substantially perpendicularly from the long axis to pass through the fracture-simulating outlet slot 16.

Typically, the fracture simulator chamber is defined within, as the inner diameter of, an elongate cylindrical tubular member. A side wall 14d of the member defines an inner diameter and the long axis x extends between open end 14b and a closed end 14c and the fracture-simulating outlet slot is positioned in the side wall. For example, the fracture simulator may be a length of pipe with an open end and an opposite closed end, with the inner diameter of the pipe forming the chamber 14a. Slot 16 is on the pipe's side wall extending from, and thereby creating an opening, from the pipe's inner surface to its outer surface. As noted, the side wall location of the slot orients the slot as perpendicular to the long axis of the pipe's inner diameter, and thereby orients the slot as perpendicular to inlet flow into the fracture simulator chamber formed by its inner diameter.

The slot, being formed through the side wall, simulates the location of a fracture in a wellbore, wherein the fracture is located on the cylindrical wellbore wall.

With reference to FIGS. 3c and 3d, photographs show a successful diversion material seal established against a fracture simulator slot. Larger diameter diversion materials (i.e. bridging agent) are initially stopped by and pack against the slot 16. After the larger diameter materials begin to bridge, then the finer diversion materials are stopped and pack against the bridging agent. Eventually, the diversion materials substantially stop fluid flow through the slot. The photos are from an actual test with one pill of diversion material. Since less than 1 cm fill was found on the bottom, the fracture simulator was operating properly with material caking on the sidewall at the slot, rather than filling the bottom. This also shows that volume of material was optimized with very little wasted product and the material creating a seal without packing the simulator chamber.

The embodiment shown in FIGS. 3a-3d tests the placement of a near wellbore seal. In particular, the diversion material is deposited on the sidewalls and in the slot, which has a minimal depth—only the thickness of the simulator wall.

For each fracture simulator, the slot characteristics, such as its dimensions L, W and orientation, are known. The width W of the slot can be selected to correlate to the width of a fracture from fracture simulation modelling. By selecting pump conditions, the response of diversion material with respect to slot 16 can be very similar to an actual wellbore response. In one embodiment, a plurality of fracture simulators, each having a slot width differing by 1 mm increments with widths between 1 mm and 11 mm. The slot is generally free of screen so that the bridging effect can be correlated to the slot characteristics.

The length L can be varied, but in one embodiment it is maintained standard since the fracture length has relatively lower impact on diversion material activity in wellbore operations than other slot characteristics such as width.

The orientation, which means placement and orientation of the length L relative to axis, can be also be varied.

For example, while only one slot 16 is shown the embodiment of FIG. 3a, a fracture simulator may include more than one slot. To simulate a wellbore condition, in one embodiment, there may be a second slot similar to slot 16 but positioned diametrically opposed on the opposite sidewall. Such a condition in a wellbore, where fractures are diametrically opposed, is known as a bi-wing (or bi-planar) frac.

Figure 4A:
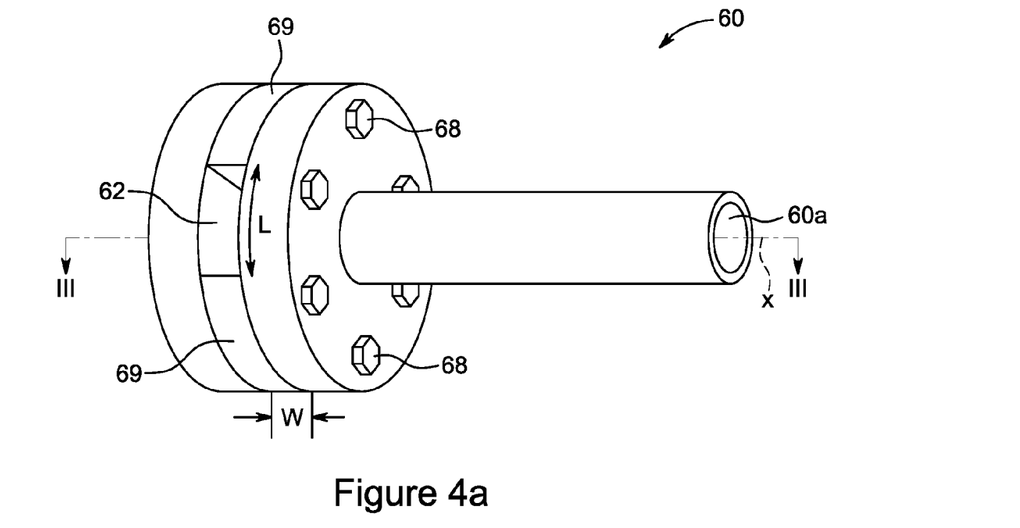
FIG. 4*a* is an isometric view of another fracture simulator.
Figure 4B:
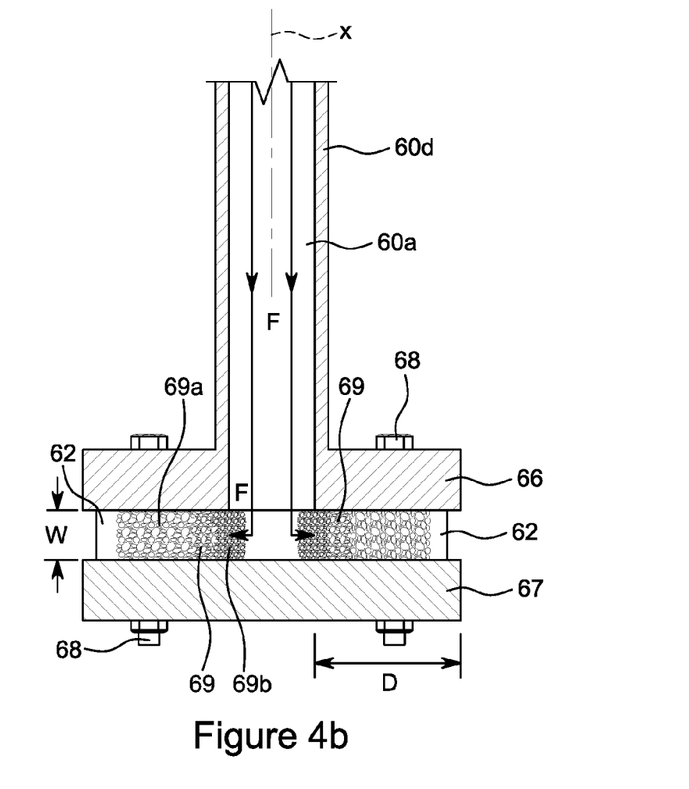
FIG. 4*b* is a sectional view along line of FIG. 4*a* with an amount of diversion material bridged in the fracture simulator.

An embodiment with a bi-wing slot orientation is shown in FIGS. 4a and 4b. In this embodiment, fracture simulator 60 includes two slots 62 diametrically opposed across the diameter of chamber 60a.

The embodiment of FIGS. 4a and 4b also show another option for orientation wherein slots are formed with their lengths extending more circumferentially, substantially orthogonal relative to axis x. For example, each slot 62 has a length that extends about a portion of the circumference of the side wall 60d, while the width of the slot extends axially. This is different than the slots 16 of FIGS. 1, 2 and 3b, which extend with their lengths oriented axially, substantially parallel to the long axis x.

The embodiment of FIGS. 4a and 4b offers an adjustability to select for slot dimensions wherein the slot is formed by a radial flange 66 and an end plate 67 or second flange that is adjustably connected to the radial flange. The width W of the slots is determined by the proximity of end plate 67 to flange 66 and this proximity can be adjusted by fasteners 68 and/or spacers 69. Spacers 69 can be configured, such as being pie-shaped, to each block a segment of the gap between flange 66 and end plate 67 and the open areas between the spacers are the slots. If it is desired to have a slot spanning substantially the full circumference of the side wall, the spacers can be eliminated or reduced significantly in size. In such an embodiment, the slot dimensions can be adjusted to simulate the fracture profiles regarding fracture width and orientation.

Flow through the fracture simulator is shown by arrows F. It will be appreciated, the slots remain on the side wall such that flow passing through the must be diverted perpendicularly to pass through slots in the same way that flow in a wellbore must change direction from axial flow to perpendicular flow to pass through wellbore fractures.

In the embodiment of FIGS. 4a/4b, the fracture simulator also offers a slot characteristic with respect to slot depth D. As such, while the embodiments of FIGS. 1 to 3b have a slot depth limited by the thickness of sidewall 14c, the slots 62 of FIG. 4b have an extended depth greater than the side wall thickness more similar to the wellbore fracture profile, in particular simulating partial fracture half depth. This fracture simulator construction offers selection based on the third dimension of depth. With such a construction, the depth of the bridge formed by any particular diversion material can be determined for any slot width, as may be useful for volumetric calculations related to field applications. In contrast, the embodiment shown in FIGS. 3a-3d tests the placement of a near wellbore diversion material seal. In particular, the diversion material is deposited on the sidewalls and in the slot, which has a minimal depth—only the thickness of the simulator wall.

One or both of the parallel surfaces of slots 62 formed by flange 66 and end plate FIGURE 67 can have different tolerances and/or surface roughening to simulate downhole fracturing conditions such as rock properties, permit testing of back pressure effects. Alternately or in addition, the flange 66 and/or end plate may be made of clear material to permit visualization of the bridging and diverter activity as a performance result.

FIG. 4b illustrates a diverter bridge 69 be formed in each slot 62. Generally, larger diameter particles 69a begin to catch in the gap forming slot 62 and then smaller diameter particles are forced by continued flow, arrows F, through slots 62 to pack in behind the larger particles.

If the test fails to achieve a seal in the slots, it may be determined that the diversion material is not appropriate for the slot profile and, therefore, the fracture profile. If the test does show a pressure increase, this is indicative of the formation of a seal in the slots, and it may be determined that the diversion material is appropriate for the slot profile and therefore the fracture profile.

Figure 5A:
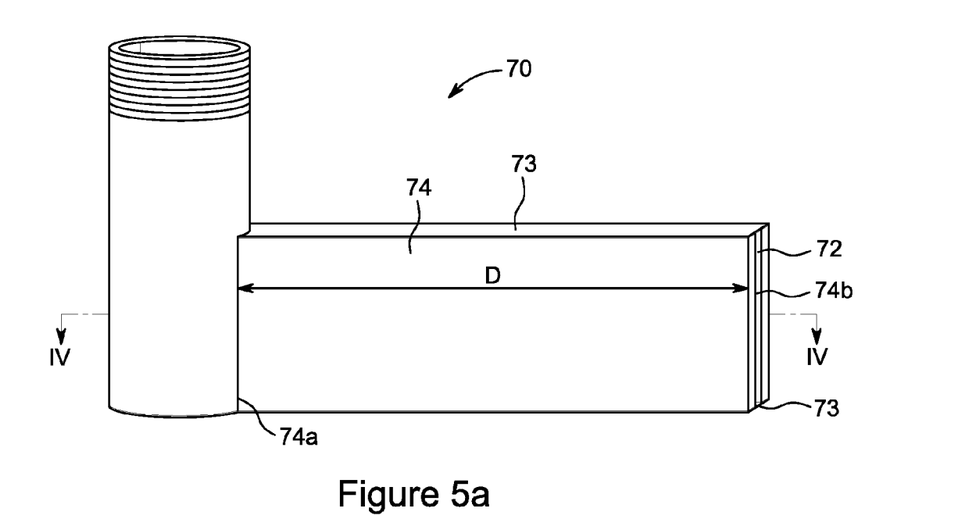
FIG. 5*a* is a side elevation of another fracture simulator.
Figure 5B:
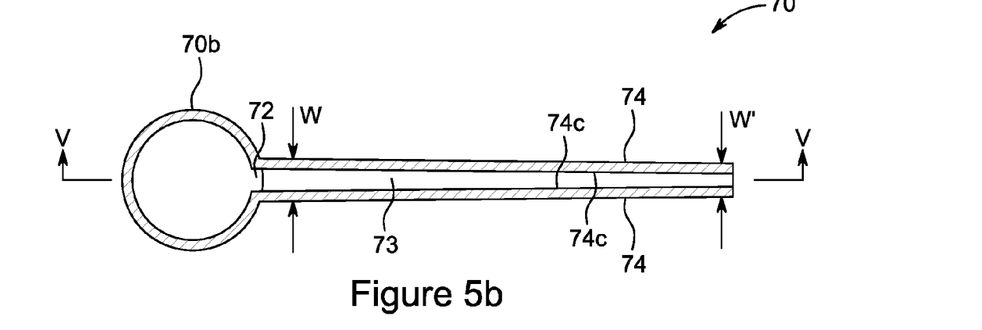
FIG. 5*b* is a sectional view along line IV-IV of FIG. 5*a;*
Figure 5C:
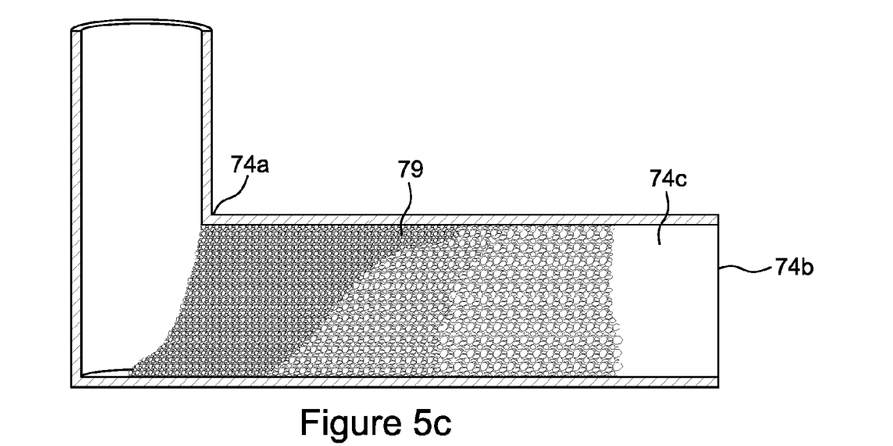
FIG. 5*c* is a sectional view along line V-V of FIG. 4*b* with an amount of diversion material bridged in the fracture simulator.

Another fracture simulator 70 that includes a structure for simulating depth of penetration is shown in FIGS. 5a-5c. While simulator 70 has an axially extending slot 72, it is similar to fracture simulator 60 in that it has a plate structure that extends the depth D of the slot. The plate structure includes a pair of plates 74 connected by solid walls 73 along the top and bottom and with a base end 74a and an open outlet end 74b. The plate structure, specifically base ends 74a of the walls, are connected in a fluid tight manner against side wall 70b of the fracture simulator encircling the slot and extend out therefrom a length to define depth D.

To simulate a fracture, the plate structure is an extension of at least the width dimension of the slot opening in side wall 70b. In other words, space between the inner facing surfaces of walls 74 is no larger than the distance between side edges of the slot opening in wall 70b. The space between facing inner surfaces of walls 74 defines width W. While width W may remain consistent along depth D, if desired, the width may taper to a narrower width W' towards open outlet end 74b as again may simulate certain wellbore fracture profiles. The width W of the slot can be selected and an apparatus may have more than one such fracture simulator, each one with a different slot W.

As noted above with respect to fracture simulator 60, the inner facing surfaces 74c of plates 74 may have surface roughness and/or the plates may be transparent to permit observation of the bridging action and the bridge 79 formed. In one embodiment, at least the inner facing surface of one or both plates are formed of the rock of the formation profile being tested.

Fracture simulator 14 of FIG. 1 also includes a structure, housing 30, to simulate fracture depth. Housing 30 is installed exteriorly about the cylindrical outer wall of simulator 14 at least encircling the area axially outside of slot 16. In the illustrated embodiment, housing 30 is installed on the inlet end of the fracture simulator or to the outlet end 12b. Housing 30 may be releasably installed. The exterior housing 30 redirects fluid and diversion material passing out through the slot and creates some back pressure which can also be controlled depending on surface roughness and distance of the gap between housing 30 and slot 16. While a fracture simulator without a housing requires a diversion material bridge to be formed at the side wall 14d, a fracture simulator with exterior housing 30 permits the diverter bridge to form at a depth. Housing 30 offers simulation with respect to the third dimension of fracture geometry: depth D. Regardless, the exterior housing includes an open outlet therefrom to permit fluid to discharge from the exterior housing. In one embodiment, the exterior housing is a pipe with a diameter larger than the pipe with slot 16 and the pipe forming the exterior housing is sleeved over the pipe with a known distance gap between the slot and the inner wall of the exterior pipe. The fracture simulator may include an exterior housing installed outside the controlled slot size. The exterior housing contains the fluid and diversion material passing through the slot and creates some back pressure which can also be controlled depending on surface roughness and distance between housing and slot. Exterior housing can be used to represent the depth of penetration of the diverter bridge. This represents the third degree of fracture geometry, length of slot or depth. This exterior housing can also include a variable width slot which allows fluid to propagate through the slot.

As with each of the fracture simulators, the releasable connection 15 on fracture simulator 14 facilitates replacement of the fracture simulator, which has a known slot profile (i.e. width, depth, surface roughness, orientation) with another simulator that has a different slot profile. An apparatus may include a number of fracture simulators, each with similar releasable connectors but different slot flow area geometry and/or orientation. The releasable connection may be a quick release fitting, flange, threads, etc.

In the method, a diversion material can be selected to cause pressure diversion for a particular fracture profile and/or fracture fluid. Diversion material particle size, such as including particle size distribution can be selected for a particular fracture profile such as fracture width, length, depth, rock roughness, orientation. Other fracturing fluid factors can be tested, such as by addition of additives to the diversion material or the fracturing fluid type to test for pressure and/or flow rate response. Alternately or in addition, the method and apparatus can test the various new or modified diversion materials such as the effects of adding various diversion materials and/or additives on dissolution time. Alternately or in addition, the method and apparatus can test the effects of adding proppant into the diversion material. Alternately or in addition, the method and apparatus can test the effects of adding solid or liquid production chemicals into the diversion material.

A possible test procedure to validate a particular diversion material as suitable to create a pressure seal against a wellbore fracture in a formation includes the following steps:

1. Determine the fracture profile of the formation and select a fracture simulator to correlate to the fracture profile—may also consider wellbore conditions such as a temperature, hydrocarbons encountered and duration of diversion seal required;
2. Characterize a diversion material to be tested (i.e. select material alone, blends, particle size distributions, with or without additives such as proppants)—selected diversion materials tested and weighed;
3. Prepare diversion materials for launching—entrain diversion materials in a carrier fluid, gel hydrate, etc. and mix to achieve a selected concentration;
4. Prime the pump and flush piping to establish baseline pressure—this may be conducted through the direct line or before pill is loaded;
5. Prepare to launch the diversion material—shut down pump and load pill, release pill into flowing fluid or select valve to open the by-pass loop through the launching chamber;
6. Launch diversion material and monitor pressure—pump fluid to launch diversion pill while monitoring/recording pressure change;
7. Pressure bleed off and remove fracture simulator;
8. Inspect the bridge formed;
9. Collect diversion material from the fracture simulator;
10. Dry and weigh the collected diversion material; and
11. Repeat as desired to test different diversion materials, additives or fracture simulator options.

If the intent of the test is to assess a plurality of pills, the test may launch a plurality of pills into the fracture simulator prior to pressure bleed off and removal of the fracture simulator.

If the intent of the test is to validate a new diversion material (i.e. particle size, chemical composition or blend), the method may not require an assessment of the fracture profile of a formation, but rather may test the new diversion material against a range of slot dimensions to observe its performance results over a range of fracture simulators and thereby characterize its activity with respect to a range of simulated wellbore conditions.

If the intent of the test is to test solubilization rate of the diversion material, the fluid contact may be maintained in the fracture simulator for a selected residence time and a plurality of tests may be performed with different residence times.

Figure 6:
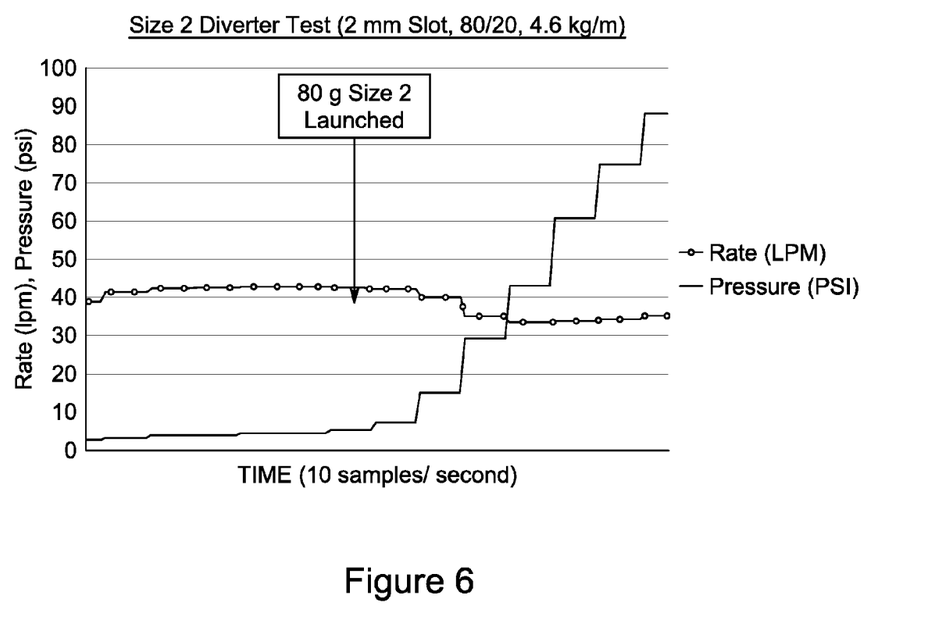
FIG. 6 is a graph showing a test result.

A successful test result is shown in FIG. 6, wherein use of the apparatus of FIG. 2 with a Type 2 diversion material successfully showed pressure diversion (i.e., full or high % blockage) of a 2 mm slot in a fracture simulator. The pressure increased to 90 psi before the control system shut down the pump.

The previous description of the disclosed embodiments is provided to enable any person skilled in the art to make or use the present invention. Various modifications to those embodiments will be readily apparent to those skilled in the art, and the generic principles defined herein may be applied to other embodiments without departing from the spirit or scope of the invention. Thus, the present invention is not intended to be limited to the embodiments shown herein, but is to be accorded the full scope consistent with the claims, wherein reference to an element in the singular, such as by use of the article "a" or "an" is not intended to mean "one and only one" unless specifically so stated, but rather "one or more". All structural and functional equivalents to the elements of the various embodiments described throughout the disclosure that are known or later come to be known to those of ordinary skill in the art are intended to be encompassed by the elements of the claims. Moreover, nothing disclosed herein is intended to be dedicated to the public regardless of whether such disclosure is explicitly recited in the claims. No claim element is to be construed under the provisions of 35 USC 112, sixth paragraph, unless the element is expressly recited using the phrase "means for" or "step for".

While illustrative embodiments have been illustrated and described, it will be appreciated that various changes can be made therein without departing from the spirit and scope of the invention.

The embodiments of the invention in which an exclusive property or privilege is claimed are defined as follows:

1. An apparatus for testing wellbore materials comprising:
   a fluid piping system including a fluid inlet end and a fluid outlet end;
   a fracture simulator chamber including a fracture-simulating outlet slot through a wall of the chamber, the fracture simulator chamber being releasably connectable to the fluid outlet end;

a pump to pump fluid through the fluid piping system from the fluid inlet line to the fluid outlet end and into the fracture simulator chamber;

a diversion material launch system connected in communication with the fluid piping system between the fluid inlet end and the fluid outlet line; and a pressure transducer in the fluid piping system to measure pressure in the fluid piping system.

2. The apparatus of claim 1 wherein the apparatus is configured to pass fluid from the fluid inlet end to the fluid outlet end, to load an amount of a diversion material from the diversion material launch system into the fluid and to move the diversion material into the fracture simulator chamber while monitoring the pressure for a pressure increase indicative of the diversion material blocking the fracture-simulating slot.

3. The apparatus of claim 1 wherein the fluid piping system further comprises a direct line and a bypass line through the diversion material launch system.

4. The apparatus of claim 1 wherein the fluid piping system includes an inlet to a chamber of the diversion material launch system and an outlet to the diversion material launch system such that fluid from the fluid piping system passes through the chamber.

5. The apparatus of claim 1 wherein the fracture simulator chamber is configured to direct fluid along a long axis and to redirect fluid substantially perpendicularly from the long axis to pass through the fracture-simulating outlet slot.

6. The apparatus of claim 1 wherein the fracture simulator chamber is an elongate tubular member with a side wall defining an inner diameter and the long axis extending between an open end and a closed end and the fracture-simulating outlet slot is positioned in a side wall.

7. The apparatus of claim 1 wherein the fracture-simulating outlet slot is rectangular including a width and a length and the length extends substantially axially along the side wall with the length substantially parallel to the long axis.

8. The apparatus of claim 1 wherein the fracture-simulating outlet slot is rectangular including a width and a length and the length extends at least partially about a circumference of the side wall.

9. The apparatus of claim 1 further comprising a second fracture-simulating outlet slot positioned on the side wall in a position substantially diametrically opposed to the fracture-simulating outlet port.

10. The apparatus of claim 1 further comprising a second fracture simulator chamber including a second fracture-simulating outlet slot differing in at least one characteristic from the fracture-simulating outlet slot and the second fracture simulator chamber being releasably connectable to the fluid outlet end as a replacement for the fracture simulator chamber.

11. The apparatus of claim 1 wherein the at least one characteristic is slot width.

12. The apparatus of claim 1 wherein the at least one characteristic is slot surface roughness.

13. The apparatus of claim 1 further comprising fracture-simulating plate extensions connected on an outer side of the fracture-simulating outlet slot, the fracture-simulating plate extensions configured to define a slot depth.

14. The apparatus of claim 1 wherein the pump is configured to pump the fluid at a rate to impart turbulence in the fluid at at least the fluid outlet end.

15. The apparatus of claim 1 further comprising a controller to monitor conditions within for the fluid piping system.

16. A method for testing the efficiency of a diversion material with respect to a wellbore fracture profile comprising:

injecting a diversion material with a known particle size through a test apparatus including through a fracture simulator; and monitoring pressure conditions in the test apparatus to identify an increase in pressure indicative of a fluid blockage formed in the fracture simulator by the diversion material.

17. The method of claim 16 wherein the fracture simulator includes a fracture-simulating outlet slot and the method further comprises selecting a fracture-simulating outlet slot configuration based on the wellbore fracture profile.

18. The method of claim 16 further comprising validating the diversion material as a possible product for fracture diversion.

19. The method of claim 16 further comprising validating a proposed fracture diversion operation based on the fluid blockage.

20. The method of claim 16 further comprising monitoring a fluid flow rate in the test apparatus.

21. The method of claim 16 wherein injecting comprises pumping a fluid through the test apparatus and loading a diversion material to the fluid.

22. The method of claim 16 wherein pumping generates turbulent flow of the fluid scaled to a hydraulic fracturing operation.

23. The method of claim 16 further comprising pumping fluid through the test apparatus to obtain a baseline pressure condition in the test apparatus prior to injecting.

24. The method of claim 16 further comprising injecting a second amount of diversion material; and continuing to monitor pressure within the test apparatus to obtain performance results.

25. The method of claim 16 wherein the pressure conditions achieved during use of the diversion material is compared with the performance results.

26. The method of claim 16 wherein the second amount of diversion material is injected onto the diversion material already in the fracture simulator.

27. The method of claim 16 further comprising replacing the fracture simulator with a second fracture simulator having a fracture parameter differing from the fracture simulator.

28. The method of claim 16 further comprising selecting a fracture simulator based on the fracture profile.

29. The method of claim 16 wherein the fracture profile includes at least one parameter selected from the group consisting of fracture width, fracture depth dimension, fracture length, fracture orientation and fracture surface roughness.

* * * * *